United States Patent
Sweazy et al.

(10) Patent No.: US 6,861,079 B2
(45) Date of Patent: Mar. 1, 2005

(54) FERTILITY KIT

(76) Inventors: Scott M. Sweazy, 1747 Village Park Dr., Orangeburg, SC (US) 29118; Jill A. Sweazy, 1747 Village Park Dr., Orangeburg, SC (US) 29118

( * ) Notice: Subject to any disclaimer, the term of this patent is extended or adjusted under 35 U.S.C. 154(b) by 0 days.

(21) Appl. No.: 10/422,882

(22) Filed: Apr. 24, 2003

(65) Prior Publication Data

US 2003/0224070 A1 Dec. 4, 2003

Related U.S. Application Data

(62) Division of application No. 10/161,271, filed on May 30, 2002, now Pat. No. 6,610,331.

(51) Int. Cl.$^7$ .......................... A61K 35/78; A61B 10/00
(52) U.S. Cl. ........................................ 424/725; 600/551
(58) Field of Search .............................. 424/725, 195.1, 424/95.1, 424; 435/906; 600/551

(56) References Cited

U.S. PATENT DOCUMENTS

| | | | | |
|---|---|---|---|---|
| 4,350,878 A | * | 9/1982 | Schwarz et al. | ........ 235/78 RC |
| 5,240,010 A | * | 8/1993 | Weinmann | ................... 600/547 |
| 5,640,968 A | * | 6/1997 | Kosasky | ...................... 600/551 |
| 5,736,144 A | * | 4/1998 | Gideon | ........................ 424/774 |

OTHER PUBLICATIONS

Horiuchi, V. Girl or Boy: Trying to Beat the Baby Odds: The Salt Lake Tribune, Aug. 1999 p. C1 accessed from Proquest direct online Jan. 15, 2004 pp. 1–4.*

* cited by examiner

Primary Examiner—Patricia Leith
(74) Attorney, Agent, or Firm—Smith Moore LLP

(57) ABSTRACT

A method and kit for enhancing the natural fertility process. The kit includes a vaginal douche that is used prior to intercourse to enhance the sperm transportation and sustaining properties of the cervical mucous. The douche contains a balanced electrolyte solution, polysaccharides, and pH buffers. The kit also includes nutriceuticals specifically formulated for both the male and female which include amino acids, minerals, vitamins, herbs, phytoestrogens, and antioxidants along with a specified dosing regimen. A basal body temperature thermometer and chart is provided with instructions to confirm when and if ovulation will/did occur. Commercially available urinary chemical reagent strips are provided with instructions so as to predict/confirm if and when ovulation will occur. A lubricating medium will also be provided and utilized at the time of intercourse which is nonspermicidal and which contains polysaccharides which influence natural sperm motility. A detailed instruction book regarding the method and practice is provided along with dietary and lifestyle recommendations which have been shown to affect natural fertility.

5 Claims, No Drawings

FERTILITY KIT

BACKGROUND OF THE INVENTION

This application is a division of utility application Ser. No. 10/161,271, filed May 30, 2002 now U.S. Pat. No. 6,610,331.

The present invention relates generally to a fertility kit used to enhance the natural fertility potential of both the male and female partner. It utilizes naturally occurring vitamins, minerals, herbs, and saccharides to assist with the normal ovulatory cycle in the female, improve the physicochemical properties of the cervical mucus, and improve the production of sperm in men along with improving the quality of the ejaculatory fluid derived from the prostate gland and seminal vesicles.

DISCUSSION OF THE RELATED ART

Approximately 15% of all married couples experience some form of infertility. Primary infertility occurs in a couple in which a child has not been successfully conceived for a period of greater than one year while performing intercourse during an appropriate schedule. Secondary infertility occurs in a couple which has previously successfully conceived and who has failed to subsequently conceive. Approximately 40% of all infertility problems are associated with a male factor, 40% are associated with a female factor, and the remaining 20% occur in couples when either both partners have an identifiable infertility cause or there is no identifiable reason in either partner that explains their infertility.

Male factor infertility may be the result of complete lack of sperm production, azoospermia, which may be the result of primary testicular failure or secondary testicular failure resulting from a previous disease such as the mumps or secondary to chemotherapy administration. Other causes include obstruction of the vas deferen or ejaculatory ducts. Greatly diminished sperm production, oligospermia, may be the result of similar problems or secondary to spermatogenic problems at the level of the testicles.

The ejaculatory fluid may be greatly diminished in patients with congenital absence of the seminal vesicles or prostate. Spinal cord lesions can also lead to retrograde ejaculation as can various surgical procedures. This results in an overall diminishment in the ejaculatory volume and the number of sperm expelled into the vaginal vault at the time of intercourse. The number, morphology, and motility of the sperm can also be greatly affected by environmental exposures such as that which occurs with cigarette smoking, alcohol intake, excessive heat exposure, and repetitive low-grade trauma to the testicles. Similar findings are seen in subfertile men with varicoceles. Super oxide free radicals can accumulate within the sperm cell, which can then cause degradation of the cellular membrane and nuclear material. Sperm injured by these intracellular oxidative radicals have a greatly reduced fertility potential.

In women, infertility problems are more difficult to detect. Primary infertility may result from bilateral ovarian agenesis, polycystic ovarian disease, congenital chromosomal abnormalities, congenital agenesis of the uterus and vaginal vault, etc. Secondary infertility may result from pelvic inflammatory disease, endometriosis, previous surgery, chemotherapy, etc. Anovulation has also been associated with an increased lean body mass ratio as seen in anorectic females and females partaking in strenuous activities/exercise. Conversely, significantly obese women are also found to be anovulatory. Intracellular oxidative free radicals also decrease the fertility potential of the egg.

Modern methods for infertility evaluation are found only in the clinical setting, typically within a medical practice. There are few books that are readily available to the public regarding information on fertility. Ovulation predictors, which are available over the counter, assess only one aspect of the fertility process and in no way enhance the natural process. To date, there is no readily available product that addresses steps which can be taken to enhance natural fertility without an exhaustive and expensive medical evaluation and treatment plan.

The current procedure in a fertility clinic includes evaluation of both the male and female partner. The male partner is evaluated with an initial sperm analysis which, if abnormal, is collected and analyzed on two additional occasions. At the same time, hormonal parameters associated with natural fertility are assessed. If the male is found to have abnormal seminal parameters with normal hormonal production, an investigation into his reproductive organs including an ultrasound of his testicles along with a prostate examination and possible ultrasound of this organ then ensue. If a varicocele is identified, this is surgically corrected. If this is not present and no obstruction is appreciated, a biopsy of the testicle is then performed. Depending upon the results of the biopsy, sperm may need to be harvested from an intratesticular site versus extratesticular sites such as the epididymis or vas deferens. This sperm would then be artificially introduced into a surgically acquired egg from the female utilizing either intracytoplasmic sperm injection versus in vitro fertilization with subsequent intrauterine or fallopian tube embryo transplantation at a later date.

If no male factor is found, the female proceeds with hormonal evaluation. If this appears normal, a transvaginal ultrasound is obtained to assess the perivaginal structures such as the uterus, fallopian tubes, and ovaries. Evidence for obstruction, endometriosis, pelvic inflammatory disease, etc., is sought. If the exam is unremarkable, a hysterosalpingogram is performed by a radiology specialist. This assesses for obstruction of the oviducts. If this is unremarkable, the female commonly undergoes a laparoscopic surgical procedure to assess for any scarring of the fimbriae of the oviduct which may preclude capture of the ruptured ovarian follicle. Any adhesions and scars are removed at that time. A post-coital test may have also been performed that assess the viability of sperm on the uterine cervix 6–12 hours following intercourse. If these factors all remain normal, the patient is then provided with an antiestrogen regimen typically consisting of clomiphene citrate and human chorionic gonadotropin which induces multiple follicles to enlarge on the ovaries. Another medication is then provided to stimulate ovulation and a washed sperm specimen is then injected into the uterus. If this fails to be successful, multiple follicles can be induced to ovulate once again. These are then surgically retrieved and cultured in-vitro with a sperm sample. Viable conceptions are then evaluated a few days later. Multiple embryos are then inserted in hopes that at least one will remain viable and develop to term. It is not unusual for the cost of these procedures to exceed well over $20,000.

Thus, there is a need for a convenient, inexpensive fertility kit that will enhance a couple's natural fertility processes. There is also a need for a kit that will provide a couple with all the material required and allow them to complete this in the privacy of their own home. There is also a need for educational material to be included within this kit so that a couple can be ensured of maximizing the natural fertility factors to their desired end.

SUMMARY OF THE PRESENT INVENTION

Accordingly, the present invention provides a method and a kit which provide a couple with the ability to maximize their fertility potential by limiting any negative environmental factors or lifestyle factors and by enhancing the natural fertility factors which influence their fertility. Moreover, all materials are provided in a conveniently utilized product which is biologically appropriate, safe to use, inexpensive, and expedient in manner and is provided in an all inclusive fertility kit.

The invention as described above, does not directly create a successful conception. It does not proceed with any artificial measures so as to induce prolonged contact of sperm with the cervical os, as which is done with other conception products, nor does it artificially induce sperm into the female reproductive tract. The fertility kit, as described, does not induce ovulation nor does it induce the maturation of multiple ovarian follicles per fertility cycle. However, the present invention enhances the natural fertility factors of the recipient, helps counteract any negative influences which might be encountered via the environment or lifestyle, and provides instructions so as to alter one's lifestyle and coital timing so as to maximize fertility potential.

DETAILED DESCRIPTION OF THE INVENTION

The present method and kit comprises an integrated program in which all aspects are used concurrently. The methodology and instructions for the practice of performing the kit are included in an instructional/informational booklet provided with this kit. This will provide the consumer with detailed instructions on how to perform and to apply each aspect of the program and the appropriate timing that this should be undertaken. Furthermore, an overview of natural fertility will be provided along with a section outlining some of the environmental factors which are commonly encountered that can negatively influence natural fertility. Additionally, recommendations so as to counteract or avoid these factors will be provided. A brief description on how each aspect of the fertility kit affects natural fertility will also be provided.

Contained in the kit will be a 30-day supply of nutriceuticals for both the male and female partner. These will be specifically formulated for each gender. Appropriate instructions for the timing and utilization of these nutriceuticals will be provided. A douche system will also be provided which will be comprised of a douche bottle(s) and applicator tip(s). The douching solution will then be provided either premixed or in a form which can be easily reconstituted with the appropriate diluent. A lubricating jelly will also be provided which will be nonspermicidal and may also have a biologically active compound(s) which may enhance the function of the sperm and/or the physiochemical properties of the cervical mucous. The lubricating jelly will be provided within a jar, tube, easy open packet, etc. Method(s) for predicting/confirming ovulation will be included; such as chemical ovulation sticks, basal body temperature thermometers and charts, salivary electrolyte monitors, etc.

The instruction booklet of the present invention will include dietary recommendations to augment the nutriceuticals. It will recommend food substances which are found to have appropriate contents of similar compounds. It will also make recommendations to avoid dietary substances such as alcohol and caffeine and over-the-counter products such as nonsteroidal anti-inflammatants which have been shown to impart a negative impact on natural fertility. Recommendations for the male to avoid exposure to high temperatures, solvents, prolonged pressure to the perineum as in bicycle riding, etc., will be discussed. For the female, the need to avoid excessive exercise, weight loss, or obesity will be discussed. The need to minimize the amount of personal stress will be discussed. The portion of the female's menstrual cycle when she is most likely to be fertile will be outlined along with the method of determining whether or not ovulation occurs with her cycle. The male will be instructed to examine his ejaculate and determine if it is of the appropriate viscosity, color, and volume which are all an indirect indicator of fertility potential.

Nutriceuticals will be consumed by both the male and the female participants. A 30-day supply for each will be provided in the kit. The combination of male ingredients includes: L-Arginine, L-Cysteine, selenium, vitamin C, vitamin E, zinc, Astragalus, Pycnogenol, and vitamin B-6. This will be taken on a daily basis for the entire 30 days. A nutriceutical which improves the natural fertility process and is comprised of L-Arginine 50–500 mg (Increase sperm count and plays a role in sperm motility); L-Cysteine 10–100 mg (Sulfur-containing amino acid needed to produce the free radical scavenger glutathione); L-Cysteine is a powerful detoxifier of alcohol, tobacco smoke, and environmental pollutants, all of which can negatively impact sperm production and sperm function); selenium 10–400 mcg (an essential component of the antioxidant enzyme glutathione peroxidase. A decreased selenium level has been associated with a decrease in sperm count and motility leading to an increase in infertility. Helps the body naturally cope with stress. Enhances vitamin E uptake.); Vitamin C 50–2000 mg (Important in sperm production. Keeps the sperm from clumping and makes them more motile. Also a very powerful antioxidant and free radical scavenger. Helps the body naturally cope with stress.); vitamin E 100 iU-1000 iU (A powerful antioxidant that prevents the oxidation of lipids and subsequently helps maintain the integrity of cellular membranes. Improves oxygenation of the sex organs. Helps the body naturally cope with stress.); Zinc 10–100 mg (Decreased seminal levels of zinc are associated with diminished semen parameters and subsequent infertility. It is a strong antioxidant and is a constituent of the antioxidant enzyme "super oxide dismutase". Helps the body naturally cope with stress.) Astragalus (Natural herb which stimulates sperm motility.); Pycnogenol 10–100 mg (Natural herbal extract containing antioxidants. Helps the body naturally cope with stress.); Vitamin B-6 10–200 mg (Required for the synthesis of RNA and DNA which is critical to the production of gametes. Influences the production of the reproductive hormones FSH and LH, both necessary to ovulation and spermatogenesis.

The female nutriceutical will consist of: selenium, vitamin C, vitamin E, zinc, Chasteberry, Dong Qui, soy, Blach Cohosh, and PABA. This will be taken for the first 15 days of the cycle. A prenatal vitamin will then be provided for the following 15 days. The douching solution will include a balanced electrolyte solution, acid buffers, saccharides, and other biologically active ingredients which may impart enhancement to sperm function or the physicochemical properties of the cervical mucus. The douche will then be utilized beginning on the fourth day prior to the time of ovulation. It will also be utilized two days prior to ovulation and at the time of ovulation. The solution will be applied intravaginally as per the instructions approximately 30 minutes prior to intercourse. Following intercourse, the female will be instructed to remain recumbent for the next two hours.

A lubricating jelly will be supplied that can be applied either intravaginally or topically. This will consist of a nonspermicidal lubricious compound which may include petroleum jelly, vegetable oil, glycerin, polycarbophil, hydroxy ethylcellulose, methylcellulose, silicone oil, carbomer, alginate, methylparaben, palm oil, cocoa butter, aloe vera, other plant oils, alginate propylene, unibase (Warner-Chilcott), mineral oil, a combination of polyethylene oxide, carboxypolymethylene, and methylparaben, and the like. Additional ingredients, such as pH stabilizers and antioxidants, may be added. Sodium hydroxide is preferably added to bring the pH to 7.4. Other pH stabilizers include EDTA or zwitterionic buffers (e.g. TES, PIPES, MOPS, HEPES). Antioxidants, or free radical scavengers such as vitamin E, may be added. The lubricant is preferably non-irritating and easily applied (see U.S. Pat. No. 6,140,121 to Ellington).

The present invention is also intended to document the natural fertility cycles of the female. Subsequently, a system (s) for ovulation prediction and detection is included. These products are well known in the industry. In general, these products detect either the increased levels of urinary luteinizing hormone (LH) which is an indirect indicator of the LH surge found in the serum which immediately precedes ovulation and induces the rupture of the mature ovarian follicle, and/or may also include a method to detect and chart the basal body temperature (BBT) of the female, which is determined first thing in the morning before arising with a temperature sensitive device such as a thermometer. This temperature is then cataloged and an appropriate graft is made during which time a typical biphasic shift in the BBT will be identified indicating that ovulation has occurred. The system(s) may also include a method of assessing the levels of salivary electrolytes which are known to change in concentration as the hormonal levels surge and shift at the time of ovulation. With this information, the female can determine if she most likely has a normal endocrine cycle indicative of a normal ovulatory cycle and also determine the period of time when she is potentially most fertile. This information can then be applied to the method and the practice employed by the kit to increase her natural fertility.

The present invention further augments the natural fertility process by allowing this to be performed in the comfort and privacy of one's own home and thus reducing the stress associated with infertility along with the stress encountered during the clinical evaluation, assessment and treatment of infertility. The cost of the product is also significantly less than the fees incurred by a fertility evaluation and associated treatment, thus enabling access to infertility assistance to an increased percentage of the population which suffers from this condition and who is otherwise unable to afford such assistance.

What is claimed is:

1. A fertility kit to enhance natural fertility and detect female ovulation and male fertility potential comprising:
   (a) Nutriceuticals, wherein said nutriceuticals comprise;
      (1) L-Arginine 50–500 mg;.
      (2) L-Cysteine 10–100 mg;
      (3) Selenium 10–400 mcg;
      (4) Vitamin C 50–2000 mg;
      (5) Vitamin E 100 iU–1000 iU;
      (6) Zinc 10–100 mg;
      (7) Astragalus;
      (8) Pycnogenol 10–100 mg;
      (9) Vitamin B-6 10–200 mg;
      (10) Para-aminobenzoic acid (PABA) 50–300 mg;
      (11) Vitamin A 1000–10,000 iU;
      (12) Folic Acid 400–1000 mcg; and
      (13) at least one phytoestrogen, wherein the at least one phytoestrogen is an isoflavone, coumestan, lignin, or any combination thereof;
   (b) Douche compound with bottle, applicator tips, pre-measured electrolytes, pH buffers, polysaccharides and monosaccharides;
   (c) A nonspermicidal lubricating jelly with polysaccharides and monosaccharides;
   (d) Ovulation predictor for determining the period of ovulation;
   (e) Basal body temperature chart and thermometer for cataloging the typical menstrual cycle for the female;
   (f) Salivary electrolyte monitor to predict and determine when ovulation will/has occurred; and
   (g) An instruction booklet outlining instructions on how to use the fertility kit along with dietary and lifestyle recommendations known to enhance fertility potential.

2. The fertility kit of claim 1:
   (a) Wherein said ovulation predictor is hormonal;
   (b) Wherein said ovulation predictor is temperature sensitive;
   (c) Wherein said ovulation predictor is a basal thermometer;
   (d) Wherein the chart will catalog basal body temperature readings over a 30-day period to catalog temperature variations known to occur with the normal menstrual cycle;
   (e) Wherein the nutriceuticals are provided either in a plastic bottle or blister pack; and
   (f) Wherein the douche is supplied with or without the diluent and with or without the additives dissolved within the diluent if provided.

3. A method for enhancing the fertility of a mammalian subject, both male and female comprising the steps of:
   (a) Adminstration of a nutriceutical supplement on a daily basis, wherein said neutriceutical supplement comprises;
      (1) L-Arginine 50–500 mg;
      (2) L-Cysteine 10–100 mg;
      (3) Selenium 10–400 mcg;
      (4) Vitamin C 50–2000 mg;
      (5) Vitamin E 100 iU–1000 iU;
      (6) Zinc 10–100 mg:
      (7) Astragalus:
      (8) Pycnogenol 10–100 mg;
      (9) Vitamin B-6 10–200 mg;
      (10) Para-aminobenzoic acid (PABA) 50–300 mg;
      (11) Vitamin A 1000–10,000 iU:
      (12) Folic Acid 400–1000 mcg; and
      (13) at least one phytoestrogen, wherein the at least one phytoestrogen is an isoflavone, coumestan, lignin, or any combination thereof;
   (b) Determining if ovulation will or has occurred with the utilization of ovulation predictor, wherein said predictor is selected from the group consisting of a hormonal predictor, a temperature sensitive predictor, or a salivary electrolyte predictor;
   (c) Determining the potential fertility of the male by describing a method through masturbation that the patient collects a semen specimen and observes it for color, viscosity, and volume;
   (d) Reconstitution and subsequent Administration of an intravaginal douche so as to improve the physicochemical characteristics of the cervical mucous along with its sperm transporting and sustaining capacity; and
   (e) Utilization of a nonspermicidal lubricating jelly with polysaccharides and/or monosaccharides to improve the fertilizing capacity of the sperm.

4. The method for enhancing the fertility of a mammalian subject of claim 3, wherein the subject is human.

5. The method for enhancing the fertility of a mammalian subject of claim 3, wherein the subject is an animal.

* * * * *

UNITED STATES PATENT AND TRADEMARK OFFICE
CERTIFICATE OF CORRECTION

PATENT NO. : 6,861,079 B2
DATED : March 1, 2005
INVENTOR(S) : Scott M. Sweazy and Jill A. Sweazy It is certified that error appears in the above-identified patent and that said Letters Patent is hereby corrected as shown below:

Column 6,
Line 33, "L-Cvsteine" should read -- L-Cysteine --.
Line 55, "Administration" should read -- administration --.
Line 59, "Utilization" should read -- Administration --.

Signed and Sealed this

Seventh Day of March, 2006

JON W. DUDAS
*Director of the United States Patent and Trademark Office*

UNITED STATES PATENT AND TRADEMARK OFFICE
CERTIFICATE OF CORRECTION

PATENT NO. : 6,861,079 B2
DATED : March 1, 2005
INVENTOR(S) : Scott M. Sweazy and Jill A. Sweazy It is certified that error appears in the above-identified patent and that said Letters Patent is hereby corrected as shown below:

<u>Column 6,</u>
Line 33, "L-Cvsteine" should read -- L-Cysteine --.
Line 55, "Administration" should read -- administration --.
Line 59, "Utilization" should read -- Administration --.

Signed and Sealed this

Fourth Day of April, 2006

JON W. DUDAS
*Director of the United States Patent and Trademark Office*